(12) United States Patent
Xu

(10) Patent No.: US 10,842,755 B2
(45) Date of Patent: Nov. 24, 2020

(54) NANOPARTICLES FOR BRAIN TARGETED DRUG DELIVERY

(71) Applicant: UNIVERSITY OF SOUTH CAROLINA, Columbia, SC (US)

(72) Inventor: Peisheng Xu, Chapin, SC (US)

(73) Assignee: University of South Carolina, Columbia, SC (US)

( * ) Notice: Subject to any disclaimer, the term of this patent is extended or adjusted under 35 U.S.C. 154(b) by 0 days.

(21) Appl. No.: 16/278,777

(22) Filed: Feb. 19, 2019

(65) Prior Publication Data
US 2019/0290592 A1 Sep. 26, 2019

Related U.S. Application Data

(60) Provisional application No. 62/647,023, filed on Mar. 23, 2018.

(51) Int. Cl.
A61K 9/51 (2006.01)
A61K 45/06 (2006.01)
(Continued)

(52) U.S. Cl.
CPC .......... *A61K 9/5153* (2013.01); *A61K 9/5115* (2013.01); *A61K 9/5176* (2013.01);
(Continued)

(58) Field of Classification Search
CPC .... A61K 9/5153; A61K 45/06; A61K 9/5192; A61K 9/5115; A61K 9/5176;
(Continued)

(56) References Cited

U.S. PATENT DOCUMENTS 4,956,188 A 9/1990 Anderson
7,446,096 B2 11/2008 Wang et al.
(Continued)

FOREIGN PATENT DOCUMENTS

CN 104840448 8/2015
WO WO 2007/037273 4/2007
WO WO 2013/052167 4/2013

OTHER PUBLICATIONS

Fang et al ,Cancer Cell Membrane-Coated Nanoparticles for Anticancer Vaccination and Drug Delivery, NanoLetters (Year: 2014).*
(Continued)

*Primary Examiner* — Carlos A Azpuru
(74) *Attorney, Agent, or Firm* — Dority & Manning, P.A.

(57) ABSTRACT

A nanoparticle suitable for delivery of an active agent across the blood-brain barrier is provided. As such, the nanoparticle can target brain tissue so that the active agent can be delivered across the blood-brain barrier to the target brain tissue. The nanoparticle includes a core that includes a core material such as a polymer or inorganic material as well as an active agent; and a shell comprising a membrane derived from a brain metastatic cancer cell, wherein the brain metastatic cancer cell facilitates transport of the nanoparticle across a blood-brain barrier. Also disclosed are methods of forming the nanoparticle and methods of using the nanoparticle.

28 Claims, 5 Drawing Sheets

(51) Int. Cl.
| | |
|---|---|
| *A61P 25/16* | (2006.01) |
| *A61P 25/18* | (2006.01) |
| *A61P 25/30* | (2006.01) |
| *A61P 35/04* | (2006.01) |
| *A61P 25/28* | (2006.01) |
| *B82Y 5/00* | (2011.01) |

(52) U.S. Cl.
CPC ............ *A61K 9/5192* (2013.01); *A61K 45/06* (2013.01); *A61P 25/16* (2018.01); *A61P 25/18* (2018.01); *A61P 25/28* (2018.01); *A61P 25/30* (2018.01); *A61P 35/04* (2018.01); *B82Y 5/00* (2013.01)

(58) Field of Classification Search
CPC .. A61K 9/5089; A61K 9/5068; A61K 31/704; A61P 25/28; A61P 25/04; A61P 25/30; A61P 25/18; A61P 25/16; B82Y 5/00
See application file for complete search history.

(56) References Cited

U.S. PATENT DOCUMENTS

| | | |
|---|---|---|
| 8,003,128 B2 | 8/2011 | Kreuter et al. |
| 8,809,277 B2 | 8/2014 | Xu et al. |
| 8,945,629 B2 | 2/2015 | Radosz et al. |
| 9,149,535 B2 | 10/2015 | Xu et al. |
| 9,168,230 B2 | 10/2015 | Xu et al. |
| 9,221,867 B2 | 12/2015 | Beliveau et al. |
| 9,283,281 B2 | 3/2016 | Xu et al. |
| 2010/0129437 A1 | 5/2010 | Gaillard |
| 2011/0305751 A1 | 12/2011 | Gaillard |
| 2012/0301512 A1 | 11/2012 | Xu et al. |
| 2014/0011760 A1 | 1/2014 | Xu et al. |
| 2014/0227185 A1 | 8/2014 | Gaillard |
| 2015/0018308 A1 | 1/2015 | Xu et al. |
| 2015/0118311 A1 | 4/2015 | Zhou et al. |
| 2015/0203586 A1 | 7/2015 | Pardridge et al. |
| 2016/0008289 A1 | 1/2016 | Xu et al. |
| 2016/0067354 A1 | 3/2016 | Xu et al. |
| 2016/0108160 A1 | 4/2016 | Xu et al. |

OTHER PUBLICATIONS

Jin et al Biomimetic Nanoparticles Camouflaged Cancer Cell Membranes and their Applications in Cancer Theranostics (Year: 2020).*
Zhai et al, Preparation and Application of Cell Membrane-Camouflaged Nanoparticles for Cancer Therapy, Theranostics, 7(10): 2575-2592. (Year: 2017).*
Al-Harthi, et al. "Amelioration of Doxorubicin-Induced Cardiotoxicity by Resveratrol" *Mol. Med. Rep.* 10 (2014) pp. 1455-1460.
Alkilany, et al. "Homing Peptide-Conjugated Gold Nanorods: The Effect of Amino Acid Sequence Display on Nanorod Uptake and Cellular Proliferation" *J. Bioconjuate Chem.* 25(6) (2014) pp. 1162-1171.
Alkilany, et al. "Gold Nanorods: Their Potential for Photothermal Therapeutics and Drug Delivery, Tempered by the Complexity of Their Biological Interactions" *Adv. Drug Delivery Rev.* 64 (2012) pp. 190-199.
Alkilany, et al. "Cellular uptake and Cytotoxicity of Gold Nanorods: Molecular Origin of Cytotoxicity and Surface Effects" *Small* 5(6) (2009) pp. 701-708.
Austin, et al. "The optical, photothermal, and facile surface chemical properties of gold and silver nanoparticles in biodiagnostics, therapy, and drug delivery" *Arch. Toxicol.* 88(7) (2014) pp. 1391-1417.
Bahadur, et al. "Multicompartment Intracellular Self-Expanding Nanogel for Targeted Delivery of Drug Cocktail" *Adv. Mater.* 24 (2012) pp. 6479-6483.
Bahadur, et al. "Design of Serum Compatible Tetrary Complexes for Gene Delivery" *Macromolecular Bioscience* 12(5) (2012) pp. 637-646.
Bauhuber, et al. "Delivery of nucleic acids via disulfide-based carrier systems" *Advanced Materials* 21 (2009) pp. 3286-3306.
Bi, et al. "Doxorubicin-Conjugated Cus Nanoparticles for Efficient Synergistic Therapy Triggered by near-Infrared Light" *Dalton Trans.* 45 (2016) pp. 5101-5110.
Biel, M.A. "Photodynamic Therapy of Head and Neck Cancers" *Photodynamic Therapy* Humana Press (2010) p. 281-293.
Blanco, et al. "Multifunctional Micellar Nanomedicine for Cancer Therapy" *Exp. Biol. Med.* 234(2) (2009) pp. 123-131.
Boulos, et al. "The Gold Nanorod-Biology Interface: From Proteins to Cells to Tissue," *J. Current Physical Chemistry* 3(2) (2013) pp. 128-135.
Boussif, et al. "A versatile vector for gene and oligonucleotide transfer into cells in culture and in vivo: Polyethylenimine" *Proceedings of the National Academy of Sciences* 92 (1995) pp. 7297-7301.
Brannon-Peppas, et al. "Nanoparticle and targeted systems for cancer therapy" *Adv Drug Deliv Rev* 56(11) (2004) pp. 1649-1659.
Brust, et al. "Synthesis of Thiol-derivatised Gold nanoparticles in a Two-phase Liquid-Liquid System" *J. Chem. Soc. Chemical Communications* 7 (1994) pp. 801-802.
Butters, et al. "Addition of drugs to a chemotherapy regimen for metastatic breast cancer" *Cochrane Database Syst Rev* 11 (2010) pp. 1-72.
Cang, et al. "Gold nanocages as contrast agents for spectroscopic optical coherence tomography" *Optics Letters* 30(22) (2005) pp. 3048-3050.
Chang, et al. "The Shape Transition of Gold Nanorods" *Langmuir* 15(3) (1998) pp. 701-709.
Chatterjee, et al. "Doxorubicin Cardiomyopathy" *Cardiology* 115 (2010) pp. 155-162.
Chen, et al. "Gold Nanocages: Engineering Their Structure for Biomedical Applications" *Advanced Materials* 17(18) (2005) pp. 2255-2261.
Cheng, et al. "Gold Nanosphere Gated Mesoporous Silica Nanoparticle Responsive to near-Infrared Light and Redox Potential as a Theranostic Platform for Cancer Therapy" *J. Biomed. Nanotechnol.* 12 (2016) pp. 435-449.
Cheng, et al. "Deep Penetration of a PDT Drug into Tumors by Noncovalent Drug-Gold Nanoparticle Conjugates" *J Am Chem Soc* 133 (2011) pp. 2583-2591.
Cheng, et al. "Highly efficient drug delivery with gold nanoparticle vectors for in vivo photodynamic therapy of cancer" *J Am Chem Soc* 130 (2008) pp. 10643-10647.
Chono, et al. "An efficient and low immunostimulatory nanoparticle formulation for systemic siRNA delivery to the tumor" *Journal of Controlled Release* 131 (2008) pp. 64-69.
Chou, T.C. "Drug Combination Studies and Their Synergy Quantification Using the Chou-Talalay Method" *Cancer Research* 70(2) (2010) pp. 440-446.
Davis, et al. "Nanoparticle therapeutics: an emerging treatment modality for cancer" *Nat Rev Drug Discov* 7(9) (2008) pp. 771-782.
Degrado, et al. "Kinetics and mechanism of hemolysis induced by melittin and by a synthetic melittin analogue" *Biophysical Journal* 37 (1982) pp. 329-338.
Dickerson, et al. "Gold nanorod assisted near-infrared plasmonic photothermal therapy (PPTT) of squamous cell carcinoma in mice" *Cancer Letters* 269(1) (2008) pp. 57-66.
Dong, et al. "Facile Synthesis of Monodisperse Superparamagnetic $Fe_3O_4$ Core@hybrid@Au Shell Nanocomposite for Bimodal Imaging and Photothermal Therapy" *Adv. Mater.* 23 (2011) pp. 5392-5397.
Dreaden, et al. "Small Molecule-Gold Nanorod Conjugates Selectively Target and Induce macrophage Cytotoxicity towards Breast Cancer Cells" *Small* 8(18) (2012) pp. 2819-2822.
Eustis, et al. "Aspect Ratio Dependence of the Enhanced Fluorescence Intensity of Gold Nanorods: Experimental and Simulation Study" *J. Phys. Chem. B* 109(34) (2005) pp. 16350-16356.
Everts, M. "Thermal scalpel to target cancer" *Expert Rev Med Devices* 4(2) (2007) pp. 131-136.
Fang, et al. "The EPR effect: Unique features of tumor blood vessels for drug delivery, factors involved, and limitations and augmentation of the effect" *Adv Drug Deliv Rev* 63 (2011) pp. 136-151.

(56) References Cited

OTHER PUBLICATIONS

Fang, et al. "Factors and mechanism of 'EPR' effect and the enhanced antitumor effects of macromolecular drugs including SMANCS" *Adv Exp Med Biol* 519 (2003) pp. 29-49.
Fazio, et al. "Laser Light Triggered Smart Release of Silibinin from a Pegylated-Plga Gold Nanocomposite" *J. Mater. Chem. B* 3 (2015) pp. 9023-9032.
Fischer, et al. "In vitro cytotoxicity testing of polycations influence of polymer structure on cell viability and hemolysis" *Biomaterials* 24 (2003) pp. 1121-1131.
Fraga, et al. "Short- and Long-Term Distribution and Toxicity of Gold Nanoparticles in the Rat after a Single-Dose Intravenous Administration" *Nanomedicine* 10 (2014) pp. 1757-1766.
Ghosh, et al. "Simultaneous and Reversible Functionalization of Copolymers for Biological Applications" *Macromolecules* 39(17) (2006) pp. 5595-5597.
Cole, et al. "Immobilization of Gold Nanorods onto Acid-Terminated Self-Assembled Monolayers via Electrostatic Interactions" *Langmuir* 20(17) (2004) pp. 7117-7122.
González-Toro, et al. "Concurrent binding and delivery of proteins and lipophilic small molecules using polymeric nanogels" *J Am Chem Soc* 134 (2012) pp. 6964-6967.
Griset, et al. "Expansile nanoparticles: synthesis, characterization, and in vivo efficacy of an acid-responsive polymeric drug delivery system" *J Am Chem Soc* 131 (2009) pp. 2469-2471.
Halig, et al. "Biodistribution Study of Nanoparticle Encapsulated Photodynamic Therapy Drugs Using Multispectral Imaging" *Proc. SPIE.* 8672 (2013) pp. 1-12.
He, et al. "Cancer cell selective-killing polymer/copper combination" *Biomaterials Science* 4(1) (2016) pp. 115-120.
Hoskin, et al. "Studies on anticancer activities of antimicrobial peptides" *Biochemica Biophysica Acta* 1778 (2008) pp. 357-375.
Ito, et al. "Hyaluronic acid and its derivative as a multi-functional gene expression enhancer: Protection from non-specific interactions, adhesion to targeted cells, and transcriptional activation" *Journal of Controlled Release* 112 (2006) pp. 382-388.
Iyer, et al. "Exploiting the enhanced permeability and retention effect for tumor targeting" *Drug Discovery Today* 11(17-18) (2006) pp. 812-818.
Jain, et al. "Plasmon Coupling in Nanorod Assemblies: Optical Absorption, Discrete Dipole Approximation Simulation, and Exciton-Coupling Model" *Am. J. Phys. Chem. B* 110(37) (2006) pp. 18243-18253.
Jana, et al. "Seed-Mediated Growth Approach for Shape-Controlled Synthesis of Spheroidal and Rod-like Gold Nanoparticles Using a Surfactant Template" *Adv. Maler.* 13(18) (2001) pp. 1389-1393.
Jana, et al. "Wet Chemical Synthesis of High Aspect Ratio Cylindrical Gold Nanorods" *J Phys. Chem. B* 105(19) (2001) pp. 4065-4067.
Jeong, et al. "Molecular design of functional polymers for gene therapy" *Progress in Polymer Science* 32 (2007) pp. 1239-1274.
Jiang, et al. "An aptamer-based biosensor for sensitive thrombin detection with phthalocyanine@ SiO2 mesoporous nanoparticles" *Biosensors & Bioelectronics* 53 (2014) pp. 340-345.
Kannan, et al. "Evidence for the Existence of a Sodium-dependent Glutathione (GSH) Transporter" *J. of Biol. Chem.* 271(16) (1996) pp. 9754-9758.
Kashiwagi, et al. "Selective sigma-2 ligands preferentially bind to pancreatic adenocarcinomas: applications in diagnostic imaging and therapy" *Molecular Cancer* 6(1):48 (2007) pp. 1-12.
Khan, et al. "Gold nanoparticles: A paradigm shift in biomedical applications" *Advances in Colloid and Interface Science* 199-200 (2013) pp. 44-58.
Khlebtsov, et al. "Biodistribution and Toxicity of Engineered Gold Nanoparticles: A Review of in Vitro and in Vivo Studies" *Chem. Soc. Rev.* 40 (2011) pp. 1647-1671.
Kwon, et al. "Proteinticle/Gold Core/Shell Nanoparticles for Targeted Cancer Therapy without Nanotoxicity" Adv. Mater. 26 (2014) pp. 6436-6441.

Lam, et al. "Photodynamic therapy-induced apoptosis in epidermoid carcinoma cells. Reactive oxygen species and mitochondrial inner membrane permeabilization" *Journal of Biological Chemistry* 276 (2001) pp. 47379-47386.
Lee, et al. "A novel pH-responsive polysaccharidic ionic complex for proapoptotic D-(KLAKLAK)2 peptide delivery" *Chemical Communication* 47 (2010) pp. 3852-3857.
Lee, et al. "Tumor pH-responsive flower-like micelles of poly(L-lactic acid)-bpoly(ethylene glycol)-b-poly(L-histidine)" *Journal of Controlled Release* 123 (2007) pp. 19-26.
Lee, et al. "Mussel-Inspired Surface Chemistry for Multifunctional Coatings" *Science* 318 (2007) pp. 426-430.
Lee, et al. "Gold and Silver Nanoparticles in Sensing and Imaging: Sensitivity of Plasmon Response to Size, Shape, and Metal Composition" *Am. J. Phys. Chem. B* 110(39) (2006) pp. 19220-19225.
Leff, et al. "Synthesis and Characterization of Hydrophobic, Organically-Soluble Gold Nanocrystals Functionalized With Primary Amines" *Langmuir* 12(20) (1996) pp. 4723-4730.
Lehár, et al. "Synergistic drug combinations tend to improve therapeutically relevant selectivity" *Nat Biotech* 27(7) (2009) pp. 659-666.
Li, et al. "Small Gold Nanorods Laden Macrophages for Enhanced Tumor Coverage in Photothermal Therapy" *Biomaterials* 74 (2016) pp. 144-154.
Lin, et al. "Dual-Enhanced Photothermal Conversion Properties of Reduced Graphene Oxide-Coated Gold Superparticles for Light-Triggered Acoustic and Thermal Theranostics" *Nanoscale* 8 (2016) pp. 2116-2122.
Link, et al. "Laser-Induced Shape Changes of Colloidal Gold Nanorods Using Femtosecond and Nanosecond Laser Pulses" *J Phys. Chem. B* 104(26) (2000) pp. 6152-6163.
Liu, et al. "Multidentate Polyethylene Glycol Modified Gold Nanorods for in Vivo near-Infrared Photothermal Cancer Therapy" *ACS Appl. Mater. Interfaces* 6 (2014) pp. 5657-5668.
Liu, et al. "Polydopamine and Its Derivative Materials: Synthesis and Promising Applications in Energy, Environmental, and Biomedical Fields" *Chem. Rev.* 114 (2014) pp. 5057-5115.
Liu, et al. "Dopamine-Melanin Colloidal Nanospheres: An Efficient Near-Infrared Photothermal Therapeutic Agent for in Vivo Cancer Therapy" *Adv. Mater.* 25 (2013) pp. 1353-1359.
Liu, et al. "Prevention of nodal metastases in breast cancer following the lymphatic migration of paclitaxel-loaded expansile nanoparticles" *Biomaterials* 34 (2013) pp. 1810-1819.
Liu, et al. "Paclitaxel-loaded expansile nanoparticles delay local recurrence in a heterotopic murine non-small cell lung cancer model" *Ann. Thorac. Surg.* 91 (2011) pp. 1077-1084.
Liu, et al. "Direct Synthesis of Pyridyl Disulfide-Terminated Polymers by RAFT Polymerization" *Macromolecular Rapid Communications* 28(3) (2007) pp. 305-314.
Loo, et al. "Nanoshell-Enabled Photonics-Based Imaging and Therapy of Cancer" Technol. *Cancer Res. Treat.* 3 (2004) pp. 33-40.
Ma, et al. "Cisplatin Compromises Myocardial Contractile Function and Mitochondrial Ultrastructure: Role of Endoplasmic Reticulum Stress" *Clin. Exp. Pharmacol. Physiol.* 37 (2010) pp. 460-465.
Mach, et al. "$\sigma_2$ receptors as potential biomarkers of proliferation in breast cancer" *Cancer Res.* 57 (1997) pp. 156-161.
MacKey, et al. "The Most Effective Gold nanorod Size for Plasmonic Photothermal Therapy: Theory and in Vitro Experiments" *J Phys. Chem, B* 118(5) (2014) pp. 1319-1326.
Maeda, H. "Tumor-selective delivery of macromolecular drugs via the EPR effect: background and future prospects" *Bioconjug Chem* 21(5) (2010) pp. 797-802.
Maeda, et al. "Tumor vascular permeability and the EPR effect in macromolecular therapeutics: a Review" *J Control Release* 65(1-2) (2000) pp. 271-284.
Master, et al. "Optimization of a Nanomedicine-Based Silicon Phthalocyanine 4 Photodynamic Therapy (Pc 4-PDT) Strategy for Targeted Treatment of EGFR-Overexpressing Cancers" *Mol Pharm.* 9(8) (2012) pp. 2331-2338.
Master, et al. "EGFR-mediated intracellular delivery of Pc 4 nanoformulation for targeted photodynamic therapy of cancer: in vitro studies" Nanomedicine 8 (2012) pp. 655-664.

(56) References Cited

OTHER PUBLICATIONS

Master, et al. "Delivery of the photosensitizer Pc 4 in PEG-PCL micelles for in vitro PDT studies" *J Pharm Sci* 99(5) (2010) pp. 2386-2398. (Abstract only).
Matsumura, et al. "Synthesis and thereto-responsive behavior of fluorescent labeled microgel particles based on poly(N-isopropylacrylamide) and its related polymers" *Polymer* 46 (2005) pp. 10027-10034.
Miles, et al. "(114c) Improving a Biopolymer through Disulfide Cross-Linking of Chitosan Polymer Chains" *AIChE Annual Meeting* (2010) (Abstract only).
Mohajer et al. "Enhanced intercellular Retention Activity of Novel pH-sensitive Polymeric Micelles in Wild and Multidrug Resistant MCF-7 Cells" *Pharmaceutical Research* 24(9) (2007) pp. 1618-1627.
Miyata, et al. "Senescence marker protein 30 has a cardio-protective role in doxorubicin-induced cardiac dysfunction" PLoS One 8:e79093 (2013) pp. 1-8.
Murphy, et al. "Controlling the Aspect Ratio of Inorganic Nanorods and Nanowires" *Advanced Materials* 14(1) (2002) pp. 80-82.
Na, et al. "Combination antitumor effects of micelle-loaded anti-cancer drugs in a CT-26 murine colorectal carcinoma model" *International Journal of Pharmaceutics* 383(1-2) (2010) pp. 192-200.
Nie, et al. "Nanotechnology applications in cancer" *Annu Rev Biomed Eng* 9 (2007) pp. 257-288.
Nieminen, et al. "A Novel Cytotoxicity Screening Assay Using a Multiwell Fluorescence Scanner" *Toxicology and Applied Pharmacology* 115 (1992) pp. 147-155. (Abstract only).
Nikoobakht, et al. "Preparation and Growth Mechanism of Gold Nanorods (NRs) Using Seed-Mediated Growth Method" *Chem. Mater.* 15 (2003) pp. 1957-1962.
Norman, et al. "Targeted Photothermal Lysis of the Pathogenic Bacteria, *Pseudomonas aeruginosa*, with Gold Nanorods" *Nano Lett.* 8(1) (2008) pp. 302-306.
Oleinick, et al. "The role of apoptosis in response to photodynamic therapy: what, where, why, and how" *Photoch Photobio Sci.* 1 (2002) pp. 1-21.
Orendorff, et al. "Aspect ratio dependence on surface enhanced Raman scattering using silver and gold nanorod substrates" *J. Physical Chemistry Chemical Physics* 8(1) (2006) pp. 165-170.
Ou, et al. "A family of bioreducible poly(disulfide amine)s for gene delivery" *Biomaterials* 30 (2009) pp. 5804-5814.
Pack, et al. "Design and Development of Polymers for Gene Delivery" *Nature Reviews* 4 (2005) pp. 581-593.
Pan, et al. "Cytolytic peptide Nanoparticles ('NanoBees') for cancer therapy" *Nanomedicine and Nanobiotechnology* 3 (2011) pp. 318-327.
Panté, et al. "Nuclear Pore Complex is Able to Transport Macromolecules with Diameters of ~39 nm" *Molecular Biology of the Cell* 13(2) (2002) pp. 425-434.
Papo, et al. "Host defense peptides as new weapons in cancer treatment" *Cellular and Molecular Life Sciences* 62 (2005) pp. 784-790.
Park, et al. "Polydopamine-Based Simple and Versatile Surface Modification of Polymeric Nano Drug Carriers" *ACS Nano.* 8(4) (2014) pp. 3347-3356.
Piao, et al. "Erythrocyte Membrane is an Alternative Coating to Polyethylene Glycol for Prolonging the Circulation Lifetime of Gold Nanocages for Photothermal Therapy" *ACS Nano.* 8 (2014) pp. 10414-10425.
Pike, et al. "Metabolism of a Disulfiram Metabolite, S-MethylN, N-Diethyldithiocarbamate, by Flavin Monooxygenase in Human Renal Microsomes" *Drug Metabolism and Disposition* 29(2) (2001) pp. 127-132.
Pridgen, et al. "Biodegradable, polymeric nanoparticle delivery systems for cancer therapy" *Nanomedicine (Land)* 2(5) (2007) pp. 669-680.
Prigodich, et al. "Multiplexed Nanoflares: mRNA Detection in Live Cells" *Analytical Chemistry* 84(4) (2012) pp. 2062-2066.

Prigodich, et al. "Nano-flares for mRNA Regulation and Detection," *Am. Chem. Soc. Nano* 3(8) (2009) pp. 2147-2152.
Rahman, et al. "Highly temperature responsive core-shell magnetic particles: Synthesis, characterization and colloidal properties" *Journal of Colloid and Interface Science* 360 (2011) pp. 556-564.
Ren, et al. "Charge Density and Molecular Weight of Polyphosphoramidate Gene Carrier are Key Parameters Influencing Its DNA Compaction Ability and Transfection Efficiency" *Biomacromolecules* 11 (2010) pp. 3432-3439.
Ryu, et al. "Surface-Functionalizable Polymer Nanogels with Facile Hydrophobic Guest Encapsulation Capabilities" *Journal of the American Chemical Society* 132 (2010) pp. 8246-8247.
Schafer, et al. "Redox environment of the cell as viewed through the redox state of the glutathione disulfide/glutathione couple" *Free Radical Biology and Medicine* 30 (2001) pp. 1191-1212.
Schmaljohann, D. "Thermo- and pH-responsive polymers in drug delivery" *Advanced Drug Delivery Reviews* 58 (2006) pp. 1655-1670.
Sivapalan, et al. "Off-Resonance Surface-Enhanced Raman Spectroscopy from Gold Nanorod Suspensions as a Function of Aspect Ratio: Not What We Thought" *J. Am. Chem. Soc. Nano* 7(3) (2013) pp. 2099-2105.
Skrabalak, et al. "Gold Nanocages for Biomedical Applications" *Adv. Mater.* 19 (2007) pp. 3177-3184.
Skrabalak, et al. "Facile synthesis of Ag nanocubes and Au nanocages" *Nature Protocols* 2(9) (2007) pp. 2182-2190.
Soman, et al. "Molecularly targeted nanocarriers deliver the cytolytic peptide melittin specifically to tumor cells in mice, reducing tumor growth" *Journal of Clinical Investigation* 119 (2009) pp. 2830-2842.
Song, et al. "Ultrasmall Gold Nanorod Vesicles with Enhanced Tumor Accumulation and Fast Excretion from the Body for Cancer Therapy" *Adv. Mater.* 27 (2015) pp. 4910-4917.
Song, et al. "Ultra-Small Iron Oxide Doped Polypyrrole Nanoparticles for in Vivo Multimodal Imaging Guided Photothermal Therapy" *Adv. Funct. Mater.* 24 (2014) pp. 1194-1201.
Sun, et al. "Using SV119-Gold Nanocage Conjugates to Eradicate Cancer Stem Cells through a Combination of Photothermal and Chemo Therapies" *Adv. Health Mater* 3(8) (2014) pp. 1283-1291.
Sun, et al. "Multifunctional Poly(D,L-Lactide-Co-Glycolide)/Montmorillonite (Plga/Mmt) Nanoparticles Decorated by Trastuzumab for Targeted Chemotherapy of Breast Cancer" *Biomaterials* 29 (2008) pp. 475-486.
Tabor, et al, "Effect of Orientation on Plasmonic Coupling between Gold Nanorods" *Am. Chem. Soc. Nano* 3(11) (2009) pp. 3670-3678.
Tosteson, et al. "The Sting. Melittin forms channels in lipid bilayers" *Biophysical Journal* 36(1) (1981) pp. 109-116.
Turkevich, et al. "A Study of the Nucleation and Growth Processes in the Synthesis of Colloidal Gold" *Discussions of the Faraday Society* 11 (1951) pp. 55-75.
Van Der Zande, et al. "Aqueous Gold Sols of Rod-Shaped Particles" *J. Phys. Chem. B* 101(6) (1997) pp. 852-854.
Van Vlerken, et al. "Augmentation of Therapeutic Efficacy in Drug-Resistant Tumor Models Using Ceramide Coadministration in Temporal-Controlled Polymer-Blend Nanoparticle Delivery Systems" *AAPS Journal* 12(2) (2010) pp. 171-180.
Von Nessen, et al. "Thermoresponsive poly-(N-isopropylmethacrylamide) microgels: Tailoring particle size by interfacial tension control" *Polymer* 54 (2013) pp. 5499-5510.
Wang, et al. "Multi-Responsive Photothermal-Chemotherapy with Drug-Loaded Melanin-Like Nanoparticles for Synergetic Tumor Ablation" *Biomaterials* 81 (2016) pp. 114-124.
Wang, et al. "Plasmonic Copper Sulfide Nanocrystals Exhibiting Near-Infrared Photothermal and Photodynamic Therapeutic Effects" *ACS Nano* 9 (2015) pp. 1788-1800.
Wang, et al. "Scopine as a Novel Brain-Targeting Moiety Enhances the Brain Uptake of Chlorambucil" *Bioconjugate Chem.* 25 (2014) pp. 2046-2054.
Wang, et al. "SV119-Gold nanocage conjugates: a new platform for targeting cancer cells via sigma-2 receptors," *Nanoscale* 4(2) (2012) pp. 421-424.

(56) References Cited

OTHER PUBLICATIONS

Xia, et al. "An enzyme-sensitive probe for photoacoustic imaging and fluorescence detection of protease activity" *Nanoscale* 3(3) (2011) pp. 950-953.

Xu, et al. "Zwitterionic chitosan derivatives for pH-sensitive stealth coating" *Biomacromolecules* 11 (2010) pp. 2352-2358.

Xu, et al. "Gene delivery through the use of a hyaluronate-associated intracellularly degradable crosslinked polyethyleneimine" *Biomaterials* 30 (2009) pp. 5834-5843.

Xu, et al. "Intracellular drug delivery by poly(lactic-co-glycolic acid) nanoparticles, revisited" *Mol Pharm.* 6 (2009) pp. 190-201.

Xu, et al. "Targeted charge-reversal nanoparticles for nuclear drug delivery" *Angew Chem Int Ed Engl* 46(26) (2007) pp. 4999-5002.

Xu, et al. "Anticancer efficacies of cisplatin-releasing pH-responsive nanoparticles" *Biomacromolecules* 7(3) (2006) pp. 829-835.

Yang, et al. "Nanoparticle Delivery of Pooled siRNA for Effective Treatment of Non-Small Cell Lung Cancer" *Molecular Pharmaceutics* 9 (2012) pp. 2280-2289.

Yang, et al. "Systemic Delivery of siRNA via LCP Nanoparticle Efficiently Inhibits Lung Metastasis" *Molecular Therapy* 20 (2012) pp. 609-615.

Yang, et al. "Smart Drug-Loaded Polymer Gold Nanoshells for Systemic and Localized Therapy of Human Epithelial Cancer" *Adv. Mater.* 21 (2009) pp. 4339-4342.

Yang, et al. "Development of Highly Porous Large PLGA Microparticles for Pulmonary Drug Delivery" *Biomaterials* 30 (2009) pp. 1947-1953.

Yang, et al. "Barrel-Stave model or toroidal model? A case study on melittin pores" *Biophysical Journal* 81 (2001) pp. 1475-1485.

Yavuz, et al. "Gold nanocages covered by smart polymers for controlled release with near-infrared light" *Nature Materials* 8(12) (2009) pp. 935-939.

Ye, et al. Bioinspired Catecholic Chemistry for Surface Modification. *Chem. Soc. Rev.* 40 (2011) pp. 4244-4258.

Yewale, et al. "Epidermal Growth Factor Receptor Targeting in Cancer: A Review of Trends and Strategies" *Biomaterials* 34 (2013) pp. 8690-8707.

Yuan, et al. "Facile Synthesis of Highly Biocompatible Poly (2-(methacryloyloxy)ethyl phosphorylcholine)-Coated Gold nanoparticles in Aqueous Solution" *Langmuir* 22(26) (2006) pp. 11022-11027.

Zhang, et al. "Near-Infrared Light-Mediated Nanoplatforms for Cancer Thermo-Chemotherapy and Optical Imaging" *Adv. Mater.* 25 (2013) pp. 3869-3880.

Zhang, et al. "Short biodegradable polyamines for gene delivery and transfection of brain capillary endothelial cells" *Journal of Controlled Release* 143 (2010) pp. 359-366.

Zhang, et al. "Folate-Decorated Poly(Lactide-Co-Glycolide)-Vitamin E Tpgs Nanoparticles for Targeted Drug Delivery" *Biomaterials* 28 (2007) pp. 1889-1899.

Zubris, et al. "In vitro activity of Paclitaxel-loaded polymeric expansile nanoparticles in breast cancer cells" *Biomacromolecules* 14 (2013) pp. 2074-2082.

\* cited by examiner

NANOPARTICLES FOR BRAIN TARGETED DRUG DELIVERY

CROSS-REFERENCE TO RELATED APPLICATION

The present application claims priority to U.S. Provisional Application Ser. No. 62/647,023, filed on Mar. 23, 2018, the disclosure of which is incorporated by reference herein.

BACKGROUND

Due to the existence of blood brain barrier (BBB), most of the small molecules for the treatment of central neural systems (CNS) diseases cannot cross the BBB. As such, there is an urgent need for the development of efficient delivery systems for CNS drugs in order to improve the treatment of Alzheimer's disease, a traumatic brain injury, multiple sclerosis, a stroke, Parkinson's disease, a brain tumor, a spinal cord tumor, an acute spinal cord injury, HIV encephalitis, Down's syndrome, rabies, epilepsy, Huntington's disease, amyotrophic lateral sclerosis, focal cerebral ischemia, addiction, obsessive-compulsive disorder, trichotillomania, schizophrenia, bipolar disorder, autism, etc.

SUMMARY OF THE INVENTION

Objects and advantages of the invention will be set forth in part in the following description, or may be obvious from the description, or may be learned through practice of the invention. The invention will be described in greater detail below by reference to embodiments thereof illustrated in the figures.

In one particular embodiment of the present invention, a nanoparticle suitable for delivery of an active agent across the blood-brain barrier is provided. The nanoparticle includes a core comprising a core material and an active agent; and a shell comprising a membrane derived from a brain metastatic cancer cell, wherein the membrane facilitates transport of the nanoparticle across a blood-brain barrier.

In another embodiment, the core material can be a polymer, an inorganic material, or a combination thereof and can be biocompatible. For instance, the core material can include poly(lactic-co-glycolic acid), polylactic acid, polyglycolic acid, polycaprolactone, polydioxanone, polydopamine, gold, mesoporous silica, or a combination thereof.

In still another embodiment, the active agent can be a central nervous system disorder treatment agent. For example, the central nervous system disorder can be Alzheimer's disease, a traumatic brain injury, multiple sclerosis, a stroke, Parkinson's disease, a brain tumor, a spinal cord tumor, an acute spinal cord injury, HIV encephalitis, Down's syndrome, rabies, epilepsy, Huntington's disease, amyotrophic lateral sclerosis, focal cerebral ischemia, addiction, obsessive-compulsive disorder, trichotillomania, schizophrenia, bipolar disorder, or autism. Further, the active agent can include n-acetyl cysteine, pyrrolidine dithiocarbamate, disulfiram, diethyldithiocarbamate, tangeritin, resveratrol, indometacin, paclitaxel, doxorubicin, temozolomide, curcumin, carboplatin, carmustine, cisplatin, cyclophosphamide, etoposide, irinotecan, lomustine, methotrexate, procarbazine, vincristine, sulindac, or a combination thereof.

In one more embodiment, the brain metastatic cancer cell can be a metastatic breast cancer cell. For instance, the metastatic breast cancer cell can be brain metastatic MDA-MB-231-Br.

In an additional embodiment, the nanoparticle can have a diameter ranging from about 10 nanometers to about 1000 nanometers.

Also disclosed are methods of forming the nanoparticles and methods of using the nanoparticles. For instance, a nanoparticle can be formed by encapsulating a core material (e.g., a polymer, an inorganic material, or a combination thereof) with an active agent to form a core of the nanoparticle; deriving a membrane from a brain metastatic cancer cell; and coextruding the core and the membrane derived from the brain metastatic cancer cell to form the nanoparticle, wherein the membrane derived from the brain metastatic cancer cell forms a shell around the core, wherein the membrane facilitates transport of the nanoparticle across a blood-brain barrier.

In one embodiment, core material can be biocompatible and can be a polymer, an inorganic material, or a combination thereof. For example, the core material can include poly(lactic-co-glycolic acid), polylactic acid, polyglycolic acid, polycaprolactone, polydioxanone, polydopamine, gold, or mesoporous silica, or a combination thereof.

In another embodiment, the active agent can be a central nervous system disorder treatment agent. Further, the central nervous system disorder can be Alzheimer's disease, a traumatic brain injury, multiple sclerosis, a stroke, Parkinson's disease, a brain tumor, a spinal cord tumor, an acute spinal cord injury, HIV encephalitis, Down's syndrome, rabies, epilepsy, Huntington's disease, amyotrophic lateral sclerosis, focal cerebral ischemia, addiction, obsessive-compulsive disorder, trichotillomania, schizophrenia, bipolar disorder, or autism. IN addition, the active agent can include n-acetyl cysteine, pyrrolidine dithiocarbamate, disulfiram, diethyldithiocarbamate, tangeritin, resveratrol, indometacin, paclitaxel, doxorubicin, temozolomide, curcumin, carboplatin, carmustine, cisplatin, cyclophosphamide, etoposide, irinotecan, lomustine, methotrexate, procarbazine, vincristine, sulindac, or a combination thereof.

In still another embodiment, the brain metastatic cancer cell can be a metastatic breast cancer cell. For example, the metastatic breast cancer cell can be brain metastatic MDA-MB-231-Br.

In another particular embodiment, a method for delivering an active agent across a blood-brain barrier of a subject is provided. The method includes providing to the subject a nanoparticle comprising a core and a shell, wherein the core includes a core material such as a polymer, an inorganic material, or a combination thereof, and the active agent, and wherein the shell includes a membrane derived from a brain metastatic cancer cell.

In one embodiment, the core material can be biocompatible. For example, the core material can be poly(lactic-co-glycolic acid), polylactic acid, polyglycolic acid, polycaprolactone, polydioxanone, polydopamine, gold, or mesoporous silica, or a combination thereof.

In another embodiment, the active agent can be a central nervous system disorder treatment agent. Further, the central nervous system disorder can be Alzheimer's disease, a traumatic brain injury, multiple sclerosis, a stroke, Parkinson's disease, a brain tumor, a spinal cord tumor, an acute spinal cord injury, HIV encephalitis, Down's syndrome, rabies, epilepsy, Huntington's disease, amyotrophic lateral sclerosis, focal cerebral ischemia, addiction, obsessive-compulsive disorder, trichotillomania, schizophrenia, bipolar disorder, or autism. In addition, the active agent can include n-acetyl cysteine, pyrrolidine dithiocarbamate, disulfiram, diethyldithiocarbamate, tangeritin, resveratrol, indometacin, paclitaxel, doxorubicin, temozolomide, curcumin, carboplatin, carmustine, cisplatin, cyclophosphamide, etoposide, irinotecan, lomustine, methotrexate, procarbazine, vincristine, sulindac, or a combination thereof. In still another embodiment, the brain metastatic cancer cell can be a metastatic breast cancer cell. For instance, the metastatic breast cancer cell can be brain metastatic MDA-MB-231-Br.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention to one skilled in the art, including the best mode thereof, is set forth more particularly in the remainder of the specification, including reference to the accompanying figures, in which.

Figure 1:
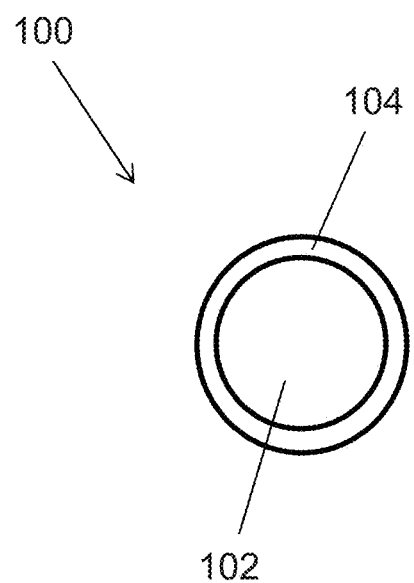
FIG. 1 is a schematic view of a nanoparticle of the present invention.

Repeat use of reference characters in the present specification and drawings is intended to represent the same or analogous features or elements of the present invention.

DETAILED DESCRIPTION

Reference now will be made to the embodiments of the invention, one or more examples of which are set forth below. Each example is provided by way of an explanation of the invention, not as a limitation of the invention. In fact, it will be apparent to those skilled in the art that various modifications and variations can be made in the invention without departing from the scope or spirit of the invention. For instance, features illustrated or described as one embodiment can be used on another embodiment to yield still a further embodiment. Thus, it is intended that the present invention cover such modifications and variations as come within the scope of the appended claims and their equivalents. It is to be understood by one of ordinary skill in the art that the present discussion is a description of exemplary embodiments only, and is not intended as limiting the broader aspects of the present invention, which broader aspects are embodied exemplary constructions.

Chemical elements are discussed in the present disclosure using their common chemical abbreviation, such as commonly found on a periodic table of elements. For example, hydrogen is represented by its common chemical abbreviation H; helium is represented by its common chemical abbreviation He; and so forth.

As used herein, the prefix "nano" refers to the nanometer scale up to about 500 nm. For example, particles having an average diameter on the nanometer scale (e.g., from about 0.1 nm to about 1000 nm) are referred to as "nanoparticles."

As used herein, the term "polymer" generally includes, but is not limited to, homopolymers; copolymers, such as, for example, block, graft, random and alternating copolymers; and terpolymers; and blends and modifications thereof. Furthermore, unless otherwise specifically limited, the term "polymer" shall include all possible geometrical configurations of the material. These configurations include, but are not limited to isotactic, syndiotactic, and random symmetries.

Generally speaking, the present invention is directed to cell membrane coated nanoparticles and a method of preparation thereof. The cell membrane coated nanoparticles can be utilized for brain targeted drug delivery, as the cell membrane coated nanoparticles have been specifically designed to effectively pass the blood brain barrier and target brain tissue. The components of the cell membrane coated nanoparticles are discussed in more detail below.

Figure 2:
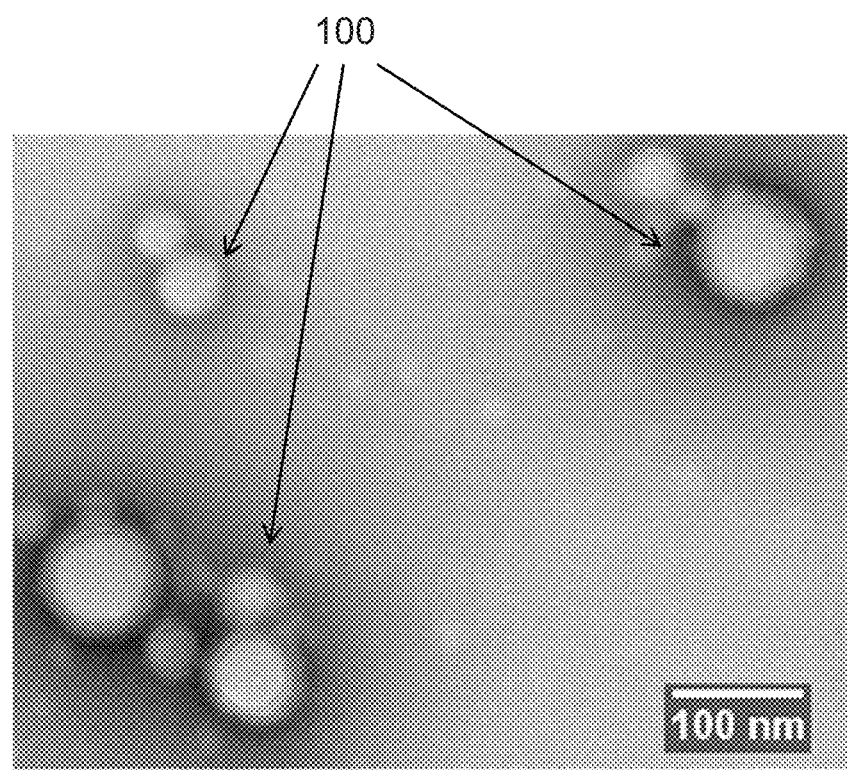
FIG. 2 is a transmission electron microscopy (TEM) image of a nanoparticle of the present invention.

Referring to FIG. 1, a schematic view of a nanoparticle 100 of the present invention is shown. Specifically, the nanoparticle 100 includes a core 102 and a shell 104. The core 102 includes a polymer and an active agent, while the shell 104 includes a membrane derived from a brain metastatic cancer cell. Specifically, the brain metastatic cancer cell component of the shell 104 facilitates transport of the active agent of the nanoparticle 100 across a blood-brain barrier to, for instance, treat a central nervous system disorder. A transmission electron microscopy (TEM) image of the nanoparticle 100 of the present invention is shown in FIG. 2. The nanoparticle 100 can have an average diameter ranging from about 0.1 nanometers to about 1000 nanometers, such as from about 10 nanometers to about 750 nanometers, such as from about 100 nanometers to about 500 nanometers. Further, the core 102 can be present in an amount ranging from about 25 wt. % to about 75 wt. %, such as from about 30 wt. % to about 70 wt. %, such as from about 40 wt. % to about 60 wt. % of the total weight of the nanoparticle 100. Meanwhile, the shell 104 can be present in an amount ranging from about 25 wt. % to about 75 wt. %, such as from about 30 wt. % to about 70 wt. %, such as from about 40 wt. % to about 60 wt. % of the total weight of the nanoparticle 100. The specific components of the nanoparticle 100 will now be described in more detail.

The material used to form the core 102 of the nanoparticle 100 can be a biocompatible material. For instance, the core material can include poly(lactic-co-glycolic acid), polylactic acid, polyglycolic acid, polycaprolactone, polydioxanone, polydopamine, gold, mesoporous silica, or a combination thereof. However it is also to be understood that any other suitable biocompatible polymer or polymer used for drug delivery as would be known by one of ordinary skill in the art is also contemplated by the present invention.

The active agent (i.e., the drug compound to be delivered to the brain) can be encapsulated into the nanoparticle by hydrophobic interaction or chemically conjugated to the surface through, e.g., —S—S—, —CONH—, or —COO— bonds. Examples of active compounds as may be delivered to target brain tissue via the nanoparticle 100 can include, without limitation, n-acetyl cysteine, pyrrolidine dithiocarbamate, disulfiram, diethyldithiocarbamate, tangeritin, resveratrol, indometacin, paclitaxel, doxorubicin, temozolomide, curcumin, carboplatin, carmustine, cisplatin, cyclophosphamide, etoposide, irinotecan, lomustine, methotrexate, procarbazine, vincristine, sulindac, etc., as well as combinations thereof.

The delivery system can be beneficial in treatment of a wide variety of CNS-related disease states including, without limitation, Alzheimer's disease, a traumatic brain injury, multiple sclerosis, a stroke, Parkinson's disease, a brain tumor, a spinal cord tumor, an acute spinal cord injury, HIV encephalitis, Down's syndrome, rabies, epilepsy, Huntington's disease, amyotrophic lateral sclerosis, focal cerebral ischemia, addiction (e.g., nicotine, controlled substances, alcohol, gambling, etc.), obsessive-compulsive disorder (e.g., nail biting and skin picking), trichotillomania, schizophrenia, bipolar disorder, or autism.

The nanoparticle 100 can formed by encapsulating the core material (e.g., a polymer or inorganic material) with an active agent to form the core 102, forming the shell 104 from a membrane derived from a brain metastatic cancer cell, and then extruding the core 102 and shell 104. For instance, to form the core 102, an emulsion method can be utilized where the active agent can be dissolved in a first solvent and an intermediate (e.g., $CH_3OH$ and an aliphatic amine such as trimethylamine) to form a first solution. Meanwhile, the core material (e.g., polymer or inorganic material) can be dissolved in a second solvent (e.g., methylene chloride) to form a second solution, after which the first solution and the second solution can be poured in to a third solution (e.g., 5% polyvinyl acetate (PVA), followed by ultrasonication for a time period ranging from about 5 minutes to about 1 hour, such as from about 10 minutes to about 45 minutes, such as about 15 minutes to about 30 minutes. Then, the resulting emulsion solution can be added to double distilled water ($ddH_2O$) and allowed to stir overnight to evaporate the organic solvent materials. Next, the remaining active agent and core material (e.g., polymer or inorganic material) can be centrifuged twice: (1) at a first speed to remove large aggregates and then at a second speed that is higher than the first speed to collect the active agent encapsulated core material nanoparticles. Then, the core material and active agent containing nanoparticles can be washed in $ddH_2O$ to remove any excess solution (e.g., excess PVA) and any non-encapsulated active agent and stored in a refrigerated environment until needed for further use. Meanwhile, the shell 104 of the nanoparticle 100 of the present invention can be formed by culturing a brain metastatic cancer cell (e.g., a brain metastatic breast cancer cell such as MDA-MB-231-Br) to the desired level of confluency and then trypsinizing the cells to remove the cells from the culture vessel in which they are cultured. Then, the cells can be centrifuged, and the resulting pellet can be resuspended in a buffer, where the cells can be homogenized. The cells can then be centrifuged again and the supernatant containing the cell membrane material can be collected and centrifuged. Then, the resulting pellet can be dispersed in phosphate buffered saline (PBS), and the extracted membranes (e.g., the shell 104 of the nanoparticle 100 of the present invention) can be extruded through a polycarbonate membrane, which can have a diameter of about 200 nanometers to about 600 nanometers (e.g., about 400 nanometers).

Thereafter, the nanoparticle 100 of the present invention can be formed by coextruding the core 102 (e.g., the core material and active agent containing nanoparticles) and the shell 104 (e.g., the brain metastatic cancer cell membranes) through a polycarbonate membrane, which can have a diameter of about 100 nanometers to about 300 nanometers (e.g., about 200 nanometers). Without intending to be limited by any particular theory, the present inventor has found that by deriving the membrane from a brain metastatic cancer cell, transport of the nanoparticle, and thus, the active agent used to treat a CNS disorder, across the blood-brain barrier is enhanced. To this end, the present invention also contemplates a method for delivering the active agent across the blood-brain barrier of a subject (e.g., a mammal). The method includes delivering the nanoparticle 100 that includes the core 102 and the shell 104 to target tissue (e.g., target brain tissue), where the membrane component of the shell 104, which is derived from a brain metastatic cancer cell, enhances the ability of the nanoparticle to cross the blood-brain barrier and reach the target tissue to be treated by the active agent.

The present invention may be better understood with reference to the Example set forth below.

EXAMPLE

1. Synthesis of Drug Loaded Poly(lactic-co-glycolic acid) (PLGA) Nanoparticle

Doxorubicin (DOX) encapsulated PLGA nanoparticle was fabricated by an emulsion method. In brief, 5 milligrams (mg) DOX was first dissolved in 1 milliliter (mL) $CH_3OH$ with 25 µL triethylamine and mixed with 5 mL $CH_2Cl_2$ containing 200 mg PLGA. The mixture solution was then poured into a 20 mL 5% polyvinyl acetate (PVA) solution on ice, followed by ultrasonication for 15 minutes (Misonix Sonicator, XL-2015, 80% power). After sonication, the emulsion solution was added into 100 mL $ddH_2O$ and stirred overnight to evaporate the organic solvent. The DOX encapsulated PLGA nanoparticle was centrifuged at 1,000 g for 10 minutes to remove big aggregates and then centrifuged at 16,000 g for 15 minutes to collect the particles. The particles were washed with $ddH_2O$ three times via a Millipore Stirred Ultrafiltration Cell (MWCO: 10,000 Da) to remove excess PVA and non-encapsulated DOX and redispersed in 10 mL $ddH_2O$ and kept at 4° C. for further use. Cy7 loaded PLGA nanoparticle was prepared similarly by replacing DOX with Cy7 during the first step.

2. Purification of the Cell Membrane from MDA-MB-231-Br Cells

To prepare cancer cell membrane vesicles, MDA-MB-231 breast cancer brain metastatic cells (MDA-MB-231-Br) were maintained in DMEM medium supplemented with 10% FBS and penicillin-streptomycin. Cells were grown in T-175 culture flasks to 90% confluency and detached with 0.05% trypsin-EDTA and centrifuged at 800 g for 5 minutes. The pellet was resuspended in hypotonic lysis buffer consisting of 1 mM $NaHCO_3$, 0.2 mM EDTA and 1 mM PMSA (1 mini protease inhibitor tablet per 10 mL of solution) and disrupted using a dounce homogenizer with a tight-fitting pestle (at least 120 passes on ice). After centrifugation at 3,200 g for 5 minutes, the supernatant was collected and centrifuged at 15,000 g for 20 minutes and the final pellet was dispersed in PBS. The extracted membranes were extruded through a 400 nanometer (nm) polycarbonate membrane for at least 22 passes. The concentration of the membrane vesicle was determined by BCA test.

3. Fabrication of the Cell Membrane Coated Nanoparticle (Brain-Meticle)

Figure 3A:
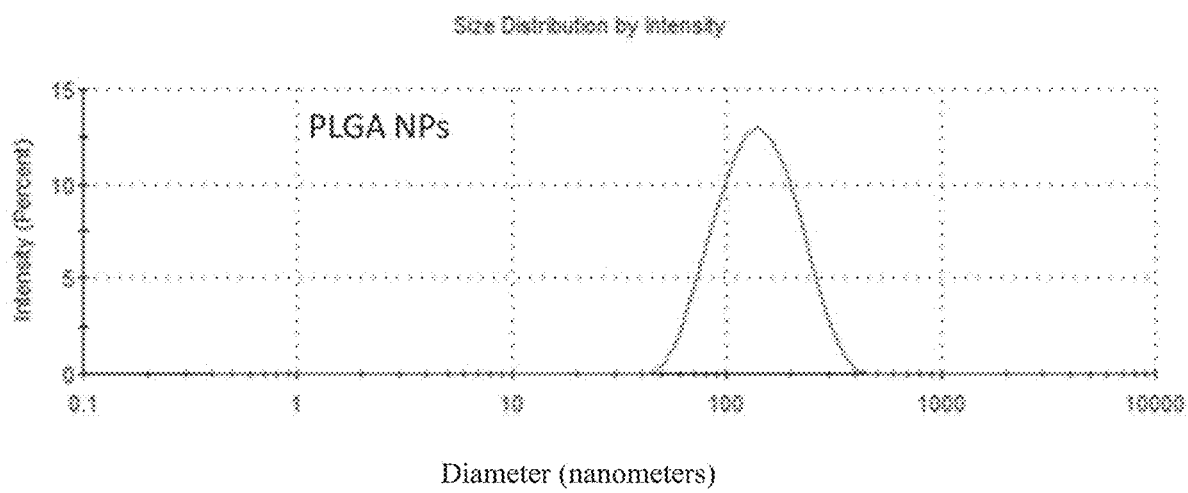
FIG. 3A is a graph showing the size distribution of poly(lactic-co-glycolic acid) (PLGA) nanoparticles.
Figure 3B:
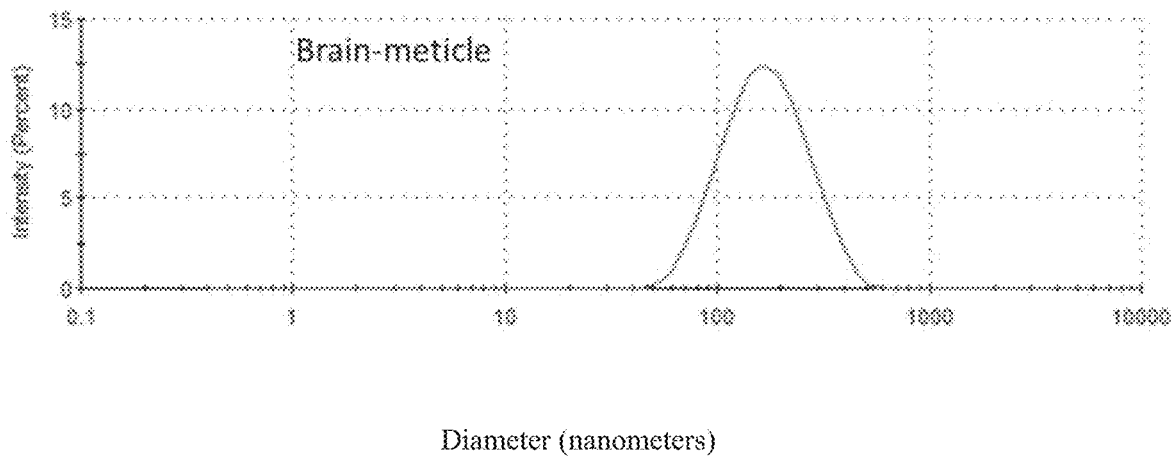
FIG. 3B is a graph showing the size distribution of the nanoparticles of the present invention.

The brain metastatic cancer cell membrane coated nanoparticle (brain-meticle) was prepared by co-extrusion of PLGA nanoparticles and cell derived membranes. PLGA nanoparticles and membrane derived particles were first mixed at 1:1 ratio (PLGA:protein, w/w) and then co-extruded through a 200 nm polycarbonate membrane. The prepared brain-meticle was stored at 4° C. for the following study. FIG. 3A shows the size distribution of poly(lacticco-glycolic acid) (PLGA) nanoparticles, while FIG. 3B showing the size distribution of the brain metastatic cancer cell membrane coated nanoparticles of the present invention.

4. Cellular Uptake of the Brain-Meticle

Figure 4:
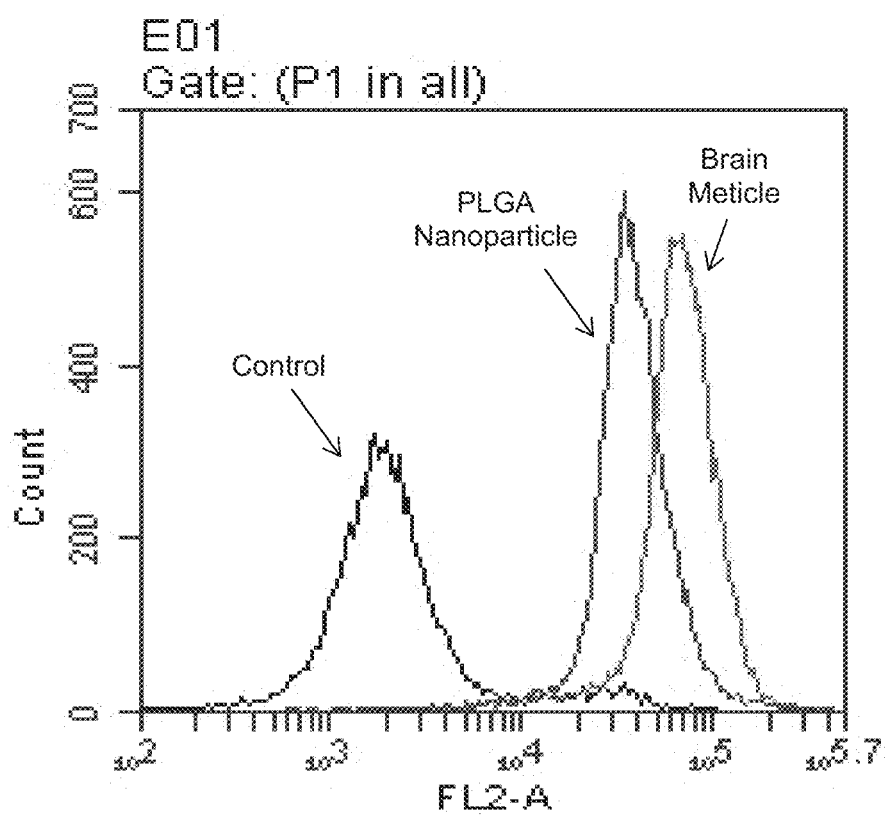
FIG. 4 is a graph illustrating the flow cytometry spectra of cellular uptake of the nanoparticles of the present invention, PLGA nanoparticles, and a control.

Cellular uptake of DOX loaded brain-meticle was determined via an animal study where MDA-MB-231-Br cells (300,000 cells/well) were seeded in 6-well plate overnight. DOX loaded PLGA nanoparticles and brain-meticle (1 mg/mL) were added and incubated for 3 hours under a humidified atmosphere of 95/5% air/CO2. Then, the cells were washed, trypsinized, and resuspended in PBS. DOX positive cell population was quantified at $\lambda ex488$ and $\lambda em585$ nm using flow cytometry (BD Accuri C6, BD Biosciences), and the results are presented in FIG. 4. As shown, the nanoparticle (e.g., the brain-meticle) of the present invention shows significant higher uptake of DOX, a chemotherapy drug often used in treating brain tumors, as compared with the plain PLGA nanoparticles.

5. In Vivo Experiments

Figure 5:
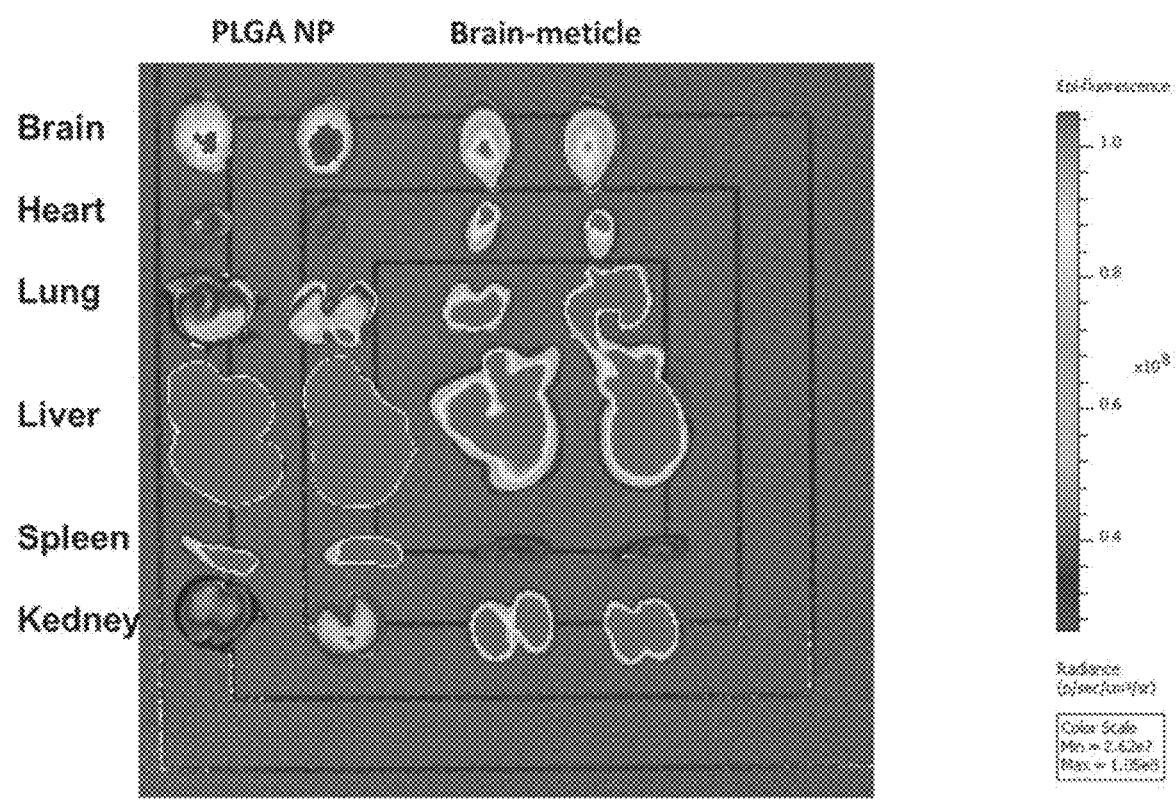
FIG. 5 illustrates fluorescence ex vivo imaging results of tissues imaged 4 hours post injection of PLGA nanoparticles and the nanoparticles of the present invention.

Animal studies were conducted under a protocol approved by the University of South Carolina Institutional Animal Care and Use Committee. C57BL/6 mice (6-8 weeks old) were purchased from Jackson laboratory. Fluorescence imaging studies were carried out 4 hours post intravenous injection (retro-orbital injection of the venous sinus) of the cy7 loaded nanoparticles of the present invention (e.g., brain-meticles) or PLGA nanoparticles, using the IVIS® Spectrum (Caliper Life Sciences). The mice were anesthetized using isoflurane and transferred to the IVIS instrument to collect full body in vivo images (Ex. 710 nm and Em.780 nm). Mice were sacrificed 4 hours post injection and the tissues including brain, spleen, heart, liver, lung, and kidneys were harvested and imaged ex vivo, as shown in FIG. 5. According to FIG. 5, the nanoparticles of the present invention were able to cross the blood-brain barrier, as evidenced by the lighter shading and increased prevalence of staining in the brain compared to the PLGA nanoparticles. In other words, less fluorescent activity was shown in the brain for the PLGA nanoparticles compared to the nanoparticles of the present invention, meaning the PLGA were not able to cross the blood-brain barrier as easily.

The embodiments of the invention described above are intended to be exemplary only. The scope of the invention is therefore intended to be limited solely by the scope of the appended claims.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed:

1. A nanoparticle comprising:
   a core comprising a core material and an active agent; and
   a shell comprising a membrane derived from a brain metastatic cancer cell, wherein the membrane facilitates transport of the nanoparticle across a blood-brain barrier, wherein the core is present in an amount ranging from about 25 wt. % to about 75 wt. % of the total weight of the nanoparticle, and wherein the shell is present in an amount ranging from about 25 wt. % to about 75 wt. % of the total weight of the nanoparticle.

2. The nanoparticle of claim 1, wherein the core material is a polymer or inorganic material, further wherein the core material is biocompatible.

3. The nanoparticle of claim 2, wherein the polymer comprises poly(lactic-co-glycolic acid), polylactic acid, polyglycolic acid, polycaprolactone, polydioxanone, or a combination thereof.

4. The nanoparticle of claim 2, wherein the inorganic material comprises polydopamine, gold, or mesoporous silica.

5. The nanoparticle of claim 1, wherein the active agent is a central nervous system disorder treatment agent.

6. The nanoparticle of claim 5, wherein the central nervous system disorder is Alzheimer's disease, a traumatic brain injury, multiple sclerosis, a stroke, Parkinson's disease, a brain tumor, a spinal cord tumor, an acute spinal cord injury, HIV encephalitis, Down's syndrome, rabies, epilepsy, Huntington's disease, amyotrophic lateral sclerosis, focal cerebral ischemia, addiction, obsessive-compulsive disorder, trichotillomania, schizophrenia, bipolar disorder, or autism.

7. The nanoparticle of claim 5, wherein the active agent comprises n-acetyl cysteine, pyrrolidine dithiocarbamate, disulfiram, diethyldithiocarbamate, tangeritin, resveratrol, indometacin, paclitaxel, doxorubicin, temozolomide, curcumin, carboplatin, carmustine, cisplatin, cyclophosphamide, etoposide, irinotecan, lomustine, methotrexate, procarbazine, vincristine, sulindac, or a combination thereof.

8. The nanoparticle of claim 1, wherein the brain metastatic cancer cell is a brain metastatic breast cancer cell.

9. The nanoparticle of claim 8, wherein the brain metastatic breast cancer cell is MDA-MB-231-Br.

10. The nanoparticle of claim 1, wherein the nanoparticle has a diameter ranging from about 10 nanometers to about 1000 nanometers.

11. A method of forming a nanoparticle, the method comprising:
    encapsulating a core material with an active agent to form a core of the nanoparticle;
    deriving a membrane from a brain metastatic cancer cell; and
    coextruding the core and the membrane derived from the brain metastatic cancer cell to form the nanoparticle, wherein the membrane derived from the brain metastatic cancer cell forms a shell around the core, wherein the membrane facilitates transport of the nanoparticle across a blood-brain barrier, wherein the core is present in an amount ranging from about 25 wt. % to about 75 wt. % of the total weight of the nanoparticle, and wherein the shell is present in an amount ranging from about 25 wt. % to about 75 wt. % of the total weight of the nanoparticle.

12. The method of claim 11, wherein the core material comprises a polymer, an inorganic material, or a combination thereof, further wherein the core material is biocompatible.

13. The method of claim 12, wherein the polymer comprises poly(lactic-co-glycolic acid), polylactic acid, polyglycolic acid, polycaprolactone, polydioxanone, or a combination thereof.

14. The method of claim 12, wherein the inorganic material comprises polydopamine, gold, or mesoporous silica.

15. The method of claim 11, wherein the active agent is a central nervous system disorder treatment agent.

16. The method of claim 15, wherein the central nervous system disorder is Alzheimer's disease, a traumatic brain injury, multiple sclerosis, a stroke, Parkinson's disease, a brain tumor, a spinal cord tumor, an acute spinal cord injury, HIV encephalitis, Down's syndrome, rabies, epilepsy, Huntington's disease, amyotrophic lateral sclerosis, focal cerebral ischemia, addiction, obsessive-compulsive disorder, trichotillomania, schizophrenia, bipolar disorder, or autism.

17. The method of claim 15, wherein the active agent comprises n-acetyl cysteine, pyrrolidine dithiocarbamate, disulfiram, diethyldithiocarbamate, tangeritin, resveratrol, indometacin, paclitaxel, doxorubicin, temozolomide, curcumin, carboplatin, carmustine, cisplatin, cyclophosphamide, etoposide, irinotecan, lomustine, methotrexate, procarbazine, vincristine, sulindac, or a combination thereof.

18. The method of claim 11, wherein the brain metastatic cancer cell is a brain metastatic breast cancer cell.

19. The method of claim 18, wherein the brain metastatic breast cancer cell is MDA-MB-231-Br.

20. A method for delivering an active agent across a blood-brain barrier of a subject, the method comprising providing to the subject a nanoparticle comprising a core and a shell, wherein the core comprises a core material and the active agent, and wherein the shell comprises a membrane derived from a brain metastatic cancer cell, wherein the core is present in an amount ranging from about 25 wt. % to about 75 wt. % of the total weight of the nanoparticle, and wherein the shell is present in an amount ranging from about 25 wt. % to about 75 wt. % of the total weight of the nanoparticle.

21. The method of claim 20, the core material is a polymer or an inorganic material, further wherein the core material is biocompatible.

22. The method of claim 21, wherein the polymer comprises poly(lactic-co-glycolic acid), polylactic acid, polyglycolic acid, polycaprolactone, polydioxanone, or a combination thereof.

23. The method of claim 21, wherein the inorganic material comprises polydopamine, gold, or mesoporous silica.

24. The method of claim 20, wherein the active agent is a central nervous system disorder treatment agent.

25. The method of claim 24, wherein the central nervous system disorder is Alzheimer's disease, a traumatic brain injury, multiple sclerosis, a stroke, Parkinson's disease, a brain tumor, a spinal cord tumor, an acute spinal cord injury, HIV encephalitis, Down's syndrome, rabies, epilepsy, Huntington's disease, amyotrophic lateral sclerosis, focal cerebral ischemia, addiction, obsessive-compulsive disorder, trichotillomania, schizophrenia, bipolar disorder, or autism.

26. The method of claim 24, wherein the active agent comprises n-acetyl cysteine, pyrrolidine dithiocarbamate, disulfiram, diethyldithiocarbamate, tangeritin, resveratrol, indometacin, paclitaxel, doxorubicin, temozolomide, curcumin, carboplatin, carmustine, cisplatin, cyclophosphamide, etoposide, irinotecan, lomustine, methotrexate, procarbazine, vincristine, sulindac, or a combination thereof.

27. The method of claim 20, wherein the brain metastatic cancer cell is a brain metastatic breast cancer cell.

28. The method of claim 27, wherein the brain metastatic breast cancer cell is MDA-MB-231-Br.

* * * * *